United States Patent [19]

Watkins et al.

[11] 4,425,503

[45] Jan. 10, 1984

[54] METHOD FOR DETECTING THE PRESENCE OF A GAS IN AN ATMOSPHERE

[75] Inventors: Wendell R. Watkins; Kenneth O. White, both of El Paso, Tex.

[73] Assignee: The United States of America as represented by the Secretary of the Army, Washington, D.C.

[21] Appl. No.: 393,223

[22] Filed: Jun. 28, 1982

Related U.S. Application Data

[63] Continuation-in-part of Ser. No. 175541, Aug. 5, 1980, abandoned.

[51] Int. Cl.$^3$ ............................................. G01N 21/26
[52] U.S. Cl. .................................................. 250/345
[58] Field of Search .................. 250/343, 345; 356/51, 356/436, 437

[56] References Cited

U.S. PATENT DOCUMENTS 4,059,356  11/1977  Kebabian ............................ 250/343

OTHER PUBLICATIONS

White et al. "Solid State Laser Wavelength Identification Using a Reference Absorber", ECOM-5820, Atmospheric Sciences Laboratory, U S Army Electronics Command, White Sands Missile Range, NM, Jun. 1977, 21 pp.

White et al., "Holmium 2.06 $\mu$m Laser Spectral Characteristics and Absorption by $CO_2$ Gas", Applied Optics, vol. 14, Jan. 1975, p. 16.

Baumgartner et al., "Continuously Tunable Ir Lidar with Applications to Remote Measurements of $SO_2$ and $CH_4$", Applied Optics, vol. 17, Nov. 15 1978, p. 3555.

White et al., "Multiwavelength Discrimantor and Display System for Solid State Lasers", Review of Scientific Instruments, vol. 47, Jun. 1976, p. 695.

White et al., "The Application of Minicomputers in Laser Atmospheric Experiments", Proceedings of IEEE, vol. 61, Nov. 1973, p. 1596.

Schleusner et al., "Solid-State Laser Wavelength Identification Using a Reference Absorber", Applied Optics, vol. 16, Oct. 1977, p. 2615.

Primary Examiner—Davis L. Willis
Attorney, Agent, or Firm—Robert P. Gibson; Anthony T. Lane; Saul Elbaum

[57]  ABSTRACT

Near real time remote sensing of atmospheric gases is performed using differential absorption lidar or transmission techniques. The wedge absorption remote sensor (WARS) utilizes an emission spike train of short time duration as is found in the long pulse output mode of a solid-state laser to define the on and off line absorption of an atmospheric gas and hence its concentration. The laser beam is split into a reference beam and a transmission beam which passes through the atmosphere being tested. The two beams are detected and amplified, and them digitized. Comparing the ratio of the digitized reference signal to transmitted signal for each spike in the spike train yields a set of transmittance values as a function of wavelength. When the digitized reference and transmitted signals are plotted, a wedge of data points results. The ratio of the upper and lower slopes of the wedge yields the absorption coefficient and concentration of the absorbing gas.

5 Claims, 4 Drawing Figures

METHOD FOR DETECTING THE PRESENCE OF A GAS IN AN ATMOSPHERE

RIGHTS OF THE GOVERNMENT

The invention described herein may be manufactured, used and licensed by or for the United States government for governmental purposes without the payment to the inventors of any royalties thereon.

This is a continuation-in-part application of Ser. No. 175,541 filed Aug. 5, 1980, now abandoned.

BACKGROUND OF THE INVENTION

This invention relates to the detection and measurement of a gas in an atmosphere, and more particularly this invention relates to the operation and use of an emission spike train as produced by a long pulse output mode of a solid-state laser as a remote sensor of atmospheric gases.

The use of lasers for the remote sensing of atmospheric gases by differential absorption techniques is already known. Lidar and transmission measurements require at present, however, that the laser source used be tunable (continuously or discretely) on and off the absorption line of the gas being sensed. It should be noted here that these tunable lasers are expensive. Also these laser sources have repetitive pulse rates as well as changes from on to off line wavelengths which are slow compared to changes in the atmosphere. The net result is a decrease in the magnitude of the signal-to-noise ratio over a measurement technique which can essentially simultaneously measure the on and off line absorption.

There is, thus, a need for a method and apparatus for the remote sensing a atmospheric gases such as methane which can utilize existing equipment and which does not require the cumbersone and expensive equipment and techniques of the prior art. The present invention has been found to satisfy this need.

SUMMARY OF THE INVENTION

The present invention has as its primary object the provision of a method for the remote sensing of atmospheric gases which is free of the aforementioned and other such disadvantages.

It is another object of the present invention to provide a method for the remote sensing of atmospheric gases utilizing presently available and relatively inexpensive equipment.

It is a further object of the present invention to provide a method for the remote sensing of atmospheric gases utilizing simple techniques.

It is still another object of the present invention to provide a method for the remote sensing of atmospheric gases wherein the presence of gases can be detected and the concentration can be determined.

It is yet another object of the present invention to provide a method for the remote sensing of atmospheric gases which is more sensitive than prior art techniques.

It is still another object of the present invention to provide a method for the remote sensing of atmospheric gases which utilizes solid-state lasers and wherein signal-to-noise ratios are minimized.

The long pulse mode operation of solid-state lasers has been shown to be useful in the near simultaneous measurement of on and off line absorption. The acquisition of the resulting data and the display techniques are generally known in the art. These characteristics have not, however, been used in the prior art to measure atmospheric gases with any degree of ease or sensitivity. The present invention, however, is based on the knowlege that a solid-state laser operated in the long pulse output mode provides an emission spike train which is then utilized to remotely measure, using differential absorption Lidar or transmission techniques, the presence and concentration of atmospheric gases. In a specific embodiment, the present invention relies on the knowledge that the spectral characteristics of the erbium and holmium lasers are such that the long pulse of these solid-state lasers contains a large number of spectrally narrow spikes of different wavelengths. Of significant importance to this invention is the use of an erbium:ytterbium-aluminum-garnet (YAG) laser to detect methane. For purposes of more easily describing the instant invention, it is denoted as the use of wedge absorption remote sensors (WARS).

The present invention relies on a basic concept of spanning an isolated absorption line of an atmospheric gas with the range of wavelengths of the spectrally narrow (typically <0.0001nm) emission spikes (typically a few usec duration and tens of spikes per train) in the spike train (typically a few m-sec duration). An optical beam splitter is used to obtain reference and transmitted beams. Signals are obtained for both beams using appropriate high speed detectors. The signals are digitized using analog-to-digital converters (ADC's). Comparing the ratio of the digitized reference signal to transmitted signal for each spike in the spike train yields a set of transmittance values as a function of wavelength. Maximum absorption and hence minimum transmittance will be experienced by the spikes which have wavelengths corresponding to the center of the absorption line. Minimum absorption and hence maximum transmittance will be experienced by the spikes which have wavelengths in the far wings of the aborption line. Hence if the digitized reference and transmitted signals coresponding to each spike are plotted on cartesian coordinates a wedge of data points results. The ratio of the upper and lower slopes of the wedge corresponds to the tramisttance of the absorption line and hence yields the absorption coefficient and concentration of the absorbing gas. The advantages of the WARS over existing differential absorption lidar and transmission techniques are several. A less expensive source (e.g. a solid-state laser operating in long pulse mode) can be used instead of a tunable laser source. Data from which gas concentration is extracted can be obtained during one pulse of the emission source (typically a few msec) during which the atmospheric changes which usually result in poor signal-to-noise ratios are minimal. This precludes having to employ costly time averaging of the on line and off line signals. Better sensitivity can be obtained with a weaker source because several long pulses can be averaged by normalizing the maximum transmittance slope to 1.0 to calibrate one set of wedge data with the next. The WARS uses similar detection and data analysis schemes to those already used in differential absorption lidar and transmittance systems.

BRIEF DESCRIPTION OF THE DRAWINGS

The invention itself will be better understood, and further features and advantages thereof will become apparent, from the following detailed description of the preferred embodiments, such description making reference to the appended drawings wherein.

DETAILED DESCRIPTION OF THE PREFERRED EMBODIMENTS

As already discussed, solid-state lasers operated in the long pulse mode typically emit a pulse which consists of a range of spectrally narrow wavelengths spanning a particular wavelength. This range of wavelengths is distributed randomly above and below the particular wavelength of concern, but is within a narrowly defined range. This distribution of spikes forms a spike train. Thus, knowing the absorption characteristics of a particular gas to be measured, an isolated absorption line of the gas can be chosen and a particular laser can be selected with an output spaning that absorption line. For instance, for measuring methane, an erbium:YAG laser having an emission at 1644.9 nm which closely coincides with the R(6) line in the $2\nu_3$ methane band (1645.1nm) is used. To detect carbon dioxide, an erbium glass or ytterbiumlithium-fluoride laser can be used. For illustrative purposes, the invention will be described by reference to the preferred embodiment wherein methane is measured. It will be quite obvious to one skilled in the art that the instant invention can find particular utility in measuring the presence of methane, and particularly methane concentration, in an emvironment wherein methane might be found, but wherein it might remain undetected until a danger is posed. Typical of such an environment would be a coal mine.

Figure 1:
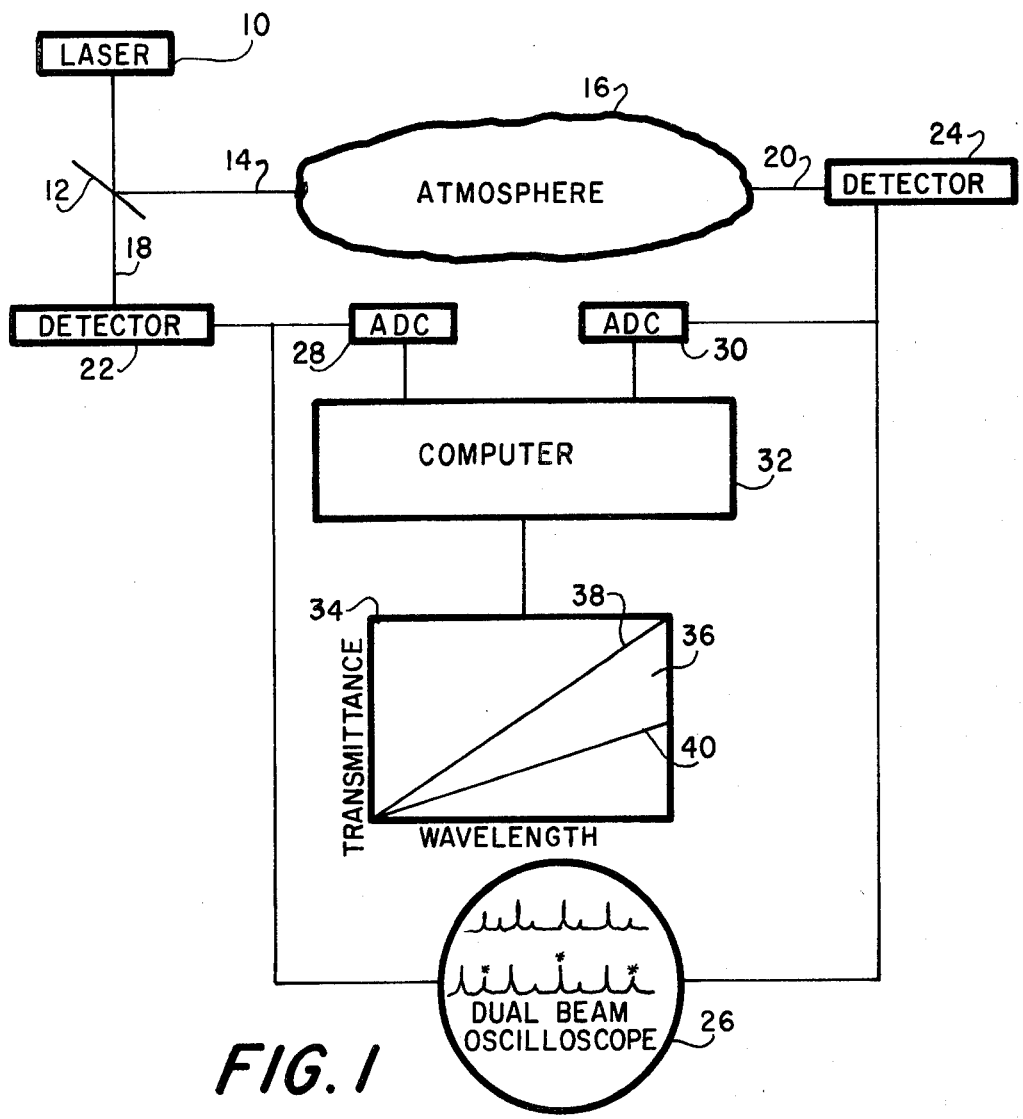
FIG. 1 is schematic diagram illustrating the apparatus used and the sequence of steps in the method.

The particular apparatus used to practice the invention is, per se, known in the art. Referring to FIG. 1, the erbium:YAG laser with an emission at about 1644.9 nm is designated by the number 10. This laser is the emission source for the spike train. It should be noted that when the laser rod is new it will span the methane absorption line. In actual system use, as the laser rod ages, there may be some drift and an intracavity etalon may be needed. The long pulse mode of the laser 10 produced a spike train of aproximately 100 spikes, each of 4 usec duration, within a time span of 4 msec. The source beam was split into two portions by an optical flat 12 with one side anti-reflection coated to eliminate secondary reflections. The major portion of the beam, designated 14, from the beam splitter 12, is propagated through the atmosphere 16 containing the absorbing gas which, in this case, is methane. For controlled tests and calibration, the propagating atmosphere is contained in an absorption cell of known part length, such absorption cells being well-known in the art. For use in an environment wherein an absorption cell cannot be used, it is sufficient merely to determine the actual path length. The reference beam 18 and the transmitted beam 20 are each directed at an indium arsenide detector, designated 22 and 24, respectively. The signals from the detectors 22 and 24 are amplified, by means not shown to typically 2 to 10 volt levels and, depending on the application, the reference signal may have to be delayed, by means not shown to compensate for the optical delay experienced by the transmitted beam over the optical path 16. Means for accomplishing both the amplification and the delay are well-known in the art. In the particular device used by applicants, Ortec 450 amplifiers were used to amplify both detector signals. The amplified signals for the reference and transmitted spike trains can be observed on a dual beam oscilloscope 26. Adjustments can then be made to insure the proper amplification and delay. The traces of the oscilloscope represent a differential absorption transmission system application. The lower trace is the transmitted spike train with varying amounts of absorption present in the spikes denoted in the drawing by asterisks.

In order to obtain the absorption wedge that represents the essence of the invention, the signals are digitized by high speed analog-to-digital converters 28 and 30, respectively. A suitable mini- or micro-computer 32 stores the digitized reference and transmitted signals for each spike of the spike train as a data pair. Each data pair is then displayed as a point on a pair of cartesian coordinates, with the reference signal as the X coordinate and the transmitted signal as the Y coordinate. This display is denoted in FIG. 1 as 34.

What the present applicants have surprisingly discovered is that when the points representing the data pairs are plotted, they form a wedge-shaped display 36 having an upper slope 38 and lower slope 40. Then, the upper and lower slope values can be obtained either manually or by use of appropriate apparatus. The ratio of the slopes 38 and 40 provide the transmittance for the line center absorption of the atmospheric gas being measured, in this case methane. This transmittance value can be converted to concentration of gas by calibrating the apparatus with known concentration of gas in an absorption cell. For ease in further treatment of the data, the upper slope 38, defined by the upper edge points in the absorption wedge, can be adjusted to be approximately 1.0 by appropriate adjustment of the signal amplifiers. The WARS requires that the emission source band width spans (at least the line center) an isolated absorption line but is not hampered by slowly varying broad band absorption and scattering as produced by dust and particulate matter except for extreme attenuations. The WARS, as already mentioned, is ideally suited for use in coal mining operations and is also suited to measure, for example, natural gas leaks as may be present in oil fields and gas storage areas.

Figure 2:
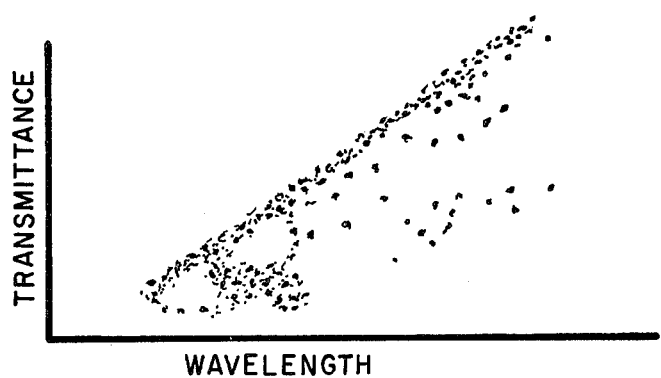
FIG. 2 is a diagram illustrating a typical display of the digitized reference and transmitted signals for a particular methane concentration showing the absorption wedge.

Referring to FIG. 2, there is shown the typical distribution of points representing the data pairs of the transmitted and reference beams, wherein the transmitted beam passed through an atmosphere containing $1.25\mu$ methane, in a 20 meter absorption cell. Initially, argon was added to the cell to 0.0343 mm. Methane was then added to 0.9680 mm. Taking the cell leak rate into account, this resulted in 1.00 mm of methane in the cell. The cell was then filled to 760 mm with argon. Readings were taken at 1 mm of methane. The cell was then evacuated to 380 mm and refilled to 760 mm with argon. Thus, the cell contained $\frac{1}{2}$ mm of methane. Readings were then taken at this methane concentration. The methane concentration was reduced for $\frac{1}{2}$ mm to $\frac{1}{4}$, $\frac{1}{8}$, 1/16, 1/32, 1/64, and finally 1/192 mm of methane. 1/192 mm corresponds to a concentration of $5\mu$. Then, the concentration was reduced by half again to $2.5\mu$ and then to $1.25\mu$. FIG. 2 is a plot of an actual photograph of the display of data points resulting from a test run comprised of data from a few laser spike trains using an atmosphere of $1.25\mu$ of methane. The resulting wedge having an upper slope and a lower slope can be clearly seen.

Figure 3:
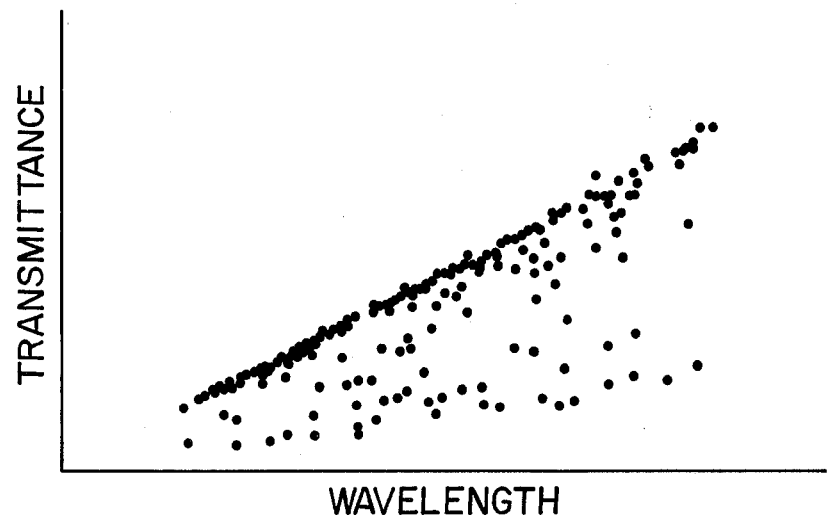
FIG. 3 is a diagram showing the reproducibility of the techniques.
Figure 4:
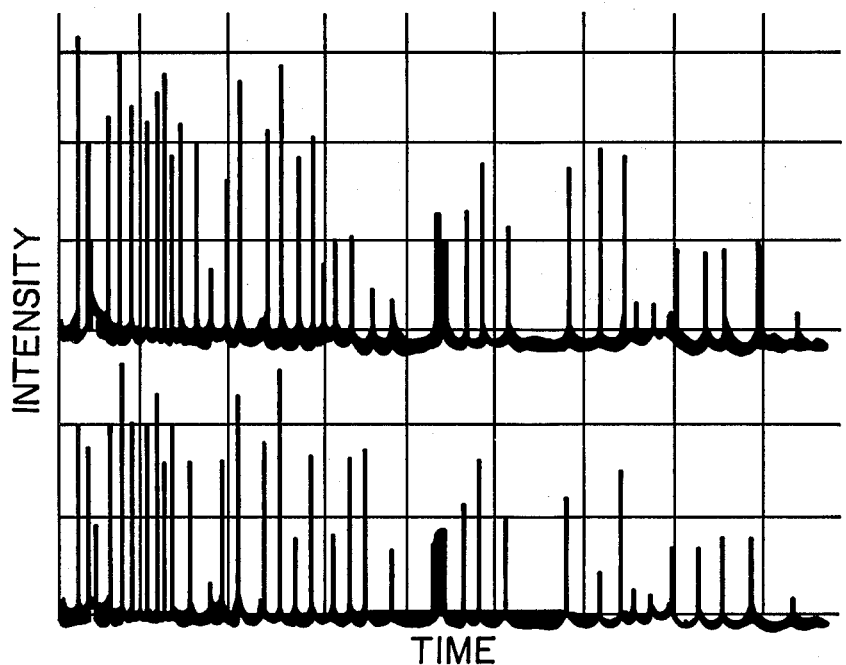
FIG. 4 is a diagram illustrating a typical display on a dual beam oscilloscope.

FIG. 3 also shows the distribution of points from another run wherein the methane concentration was 1.25μ. The reproductibility using the instant inventive method can be seen. FIG. 4 shows the reference and sample laser spikes from the same run which resulted in the data wedge shown in FIG. 3, with the lower curve in FIG. 4 being the sample signal and the upper curve being the reference signal. It should be noted that in calculating the absorption coefficient from the upper and lower slopes of the wedge, as the gas concentration rises, the lower slope drops. Thus, if the upper slope is maintained constant at 1.0 as discussed above, the ratio of the two slopes can be easily determined.

While there has been shown and described a preferred embodiment of the instant invention, those skilled in the art will appreciate that this embodiment is exemlplary and not limiting and is to be construed within the scope of the following claims.

What is claimed:

1. A method of detecting the presence of a gas in an atmosphere comprising producing a beam of a long emission pulse of a laser having a wavelength range spanning an isolated absorption line of said gas, said wavelength range comprising a plurality of spectrally narrow emission spikes, splitting said beam into a reference beam and a transmitted beam, passing said transmitted through said atmosphere, detecting each of said reference beam and the transmitted beam after passing through said atmosphere and, for each emission spike, plotting the ratio of the amplitudes of the detected transmitted beam to the reference beam, against the wavelength of the spikes, whereby the formation of a wedge of data points having an upper slope and a lower slope indicates the presence of said gas in said atmosphere.

2. A method as claimed in claim 1, further comprising determining the concentration of said gas in said atmosphere by determining the ratio of said upper slope to said lower slope to obtain the absorption coefficient and concentration of said gas.

3. A method as claimed in claim 2, further comprising selecting said upper slope to be 1.0; so that the data from several long emission pulses (containing tens of spikes each) can be averaged to obtain an accurate lower slope value and hence gas concentration.

4. A method as claimed in claim 2, wherein said gas is methane, said laser is an erbium:ytterbium-aluminum-garnet laser with emission at about 1644.9 nm, and said long pulse spans a spike train comprising about 100 spikes of about 4 usec duration per spike.

5. An apparatus for detecting the presence of a gas in an atmosphere comprising laser means for producing a beam of a long emission pulse having a wavelength range spanning an isolated absorption line of said gas, said wavelength range comprising a plurality of spectrally narrow emission spikes, means for splitting said beam into a reference beam and a transmitted beam and passing said transmitted beam through said atmosphere, means for detecting each of said reference beam and said transmitted beam after passing through said atmosphere and for producing an electrical signal, analog-to-digital converter means for converting said signals to digital signals, means for comparing the ratio of the digitized reference signal to transmitted signal for each spike in the spike train, and means for plotting the digitized transmitted signal for each spike against the digitized reference signal for each spike to thereby produce a wedge of data points having an upper slope and a lower slope, whereby the ratio of said upper and lower slopes indicates the absorption coefficient and concentration of said gas.

* * * * *